(12) United States Patent
Boldt

(10) Patent No.: US 7,109,373 B2
(45) Date of Patent: Sep. 19, 2006

(54) CREATINE SALTS AND METHOD OF MAKING SAME

(75) Inventor: Matthias Boldt, Oxnard, CA (US)

(73) Assignee: SAN Corporation, Oxnard, CA (US)

( * ) Notice: Subject to any disclaimer, the term of this patent is extended or adjusted under 35 U.S.C. 154(b) by 0 days.

(21) Appl. No.: 10/740,263

(22) Filed: Dec. 18, 2003

(65) Prior Publication Data

US 2004/0133040 A1    Jul. 8, 2004

Related U.S. Application Data

(60) Provisional application No. 60/434,245, filed on Dec. 18, 2002.

(51) Int. Cl.
*C07C 279/10*    (2006.01)

(52) U.S. Cl. .................................... 562/560

(58) Field of Classification Search ............... 562/560, 562/584
See application file for complete search history.

(56) References Cited

U.S. PATENT DOCUMENTS 5,973,199 A * 10/1999 Negrisoli et al. ........... 562/560
6,211,407 B1 * 4/2001 Thomson .................... 562/560
2003/0212136 A1   11/2003 Vonnorstrom et al.
2004/0077902 A1 * 4/2004 Llewellyn ................... 562/580

OTHER PUBLICATIONS

Dox, A.W. et al., "Esterification of Creatine", The Journal of Biological Chemistry (Oct. 1922), pp. 671-673, vol. LIV, No. 4, Pub. from the Dept. Chem. Res., Parke, Davis & Co.

* cited by examiner

*Primary Examiner*—Sikarl A. Witherspoon

(57) ABSTRACT

Disclosed are creatine salts having the general formula

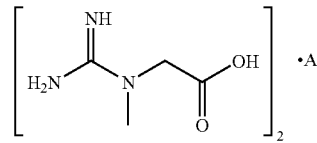

wherein A represents an anion of a dicarboxylic acid, and a process of making such salts.

13 Claims, No Drawings

CREATINE SALTS AND METHOD OF MAKING SAME

CROSS-REFERENCE TO RELATED APPLICATIONS

This application claims priority to provisional U.S. patent application No. 60/434,245, filed Dec. 18, 2002.

BACKGROUND

The embodiments relate to creatine salts and method of making such salts.

Creatine, or N-(aminoiminomethyl)-N-methylglycine, is a sarcosine derivative present in the muscle tissue of many vertebrates, including man. Creatine is a central component of the metabolic system, and is involved in the provision of energy for work and exercise performance. Phosphocreatine (also known as creatine phosphate and phosphoryl creatine) helps provide Adenosine TriPhosphate (ATP) during short bursts of high intensity exercise, and it has been found that the depletion of phosphocreatine has been associated with the onset of fatigue. It has also been discovered that the phosphocreatine pool in skeletal muscle is expandable. This has led to the oral supplementation of creatine and phosphocreatine to increase the levels of these components in muscle, to thereby enhance exercise performance during intermittent activities that require strength and power. WO 94/02127, published on Feb. 3, 1994, discloses the use of creatine, optionally combined with amino acids or other components, in order to increase the muscle performance in mammals.

Creatine is synthesized from amino acids in the liver, pancreas and kidney, by the transfer of the guanidine moiety of arginine to glycine, which is then methylated to form creatine. Creatine which is synthesized in the liver, pancreas and kidney, is released into the bloodstream and actively taken up by the muscle cells, using the Na+ gradient. Creatine oral supplementation has been used in the prior art to increase creatine and creatine phosphate stores, which are needed for high energy phosphorus metabolism. Recovery after high intensity exercise involves a resynthesis of phosphocreatine, which occurs via an oxygen-dependent process with half-life of about 30 seconds. During short-term high intensity intermittent exercise, the active muscles rely heavily on phosphocreatine for production of ATP. The rate of phosphocreatine resynthesis can be accelerated by the use of creatine supplementation in subjects who demonstrated an increase in creatine concentration. The benefits of creatine supplementation are particularly evident in high intensity activities that are intermittent in nature.

The creatine transport protein has an increased affinity for creatine and concentrates creatine within the cell. Once inside the cell, very little creatine is lost (approximately 2 grams per day in a 70 kg male). Based upon this information, it follows that small increases of plasma creatine (which can occur with creatine supplementation) result in increased transport activity. The loss of creatine from skeletal muscle is typically about 3% per day, which closely matches the amount of creatinine non-enzymatically produced by living human muscle. The main mechanism by which creatine is lost, is the conversion of creatine to creatinine, which is an irreversible non-enzymatic process. Thus, creatine lost from a cell is considered to be negligible, and the concentration of creatine in the cell is not at risk of depletion by virtue of exercise. Thus, the main advantage of creatine administration is in the fact that cellular creatine concentration is stable and not prone to being lost.

The most commonly used creatine supplement for oral consumption, is creatine monohydrate. Body builders find that shortly after beginning the use of creatine as a nutritional supplement, muscles take on additional mass and definition. Thus creatine supplements are becoming more popular as a steroid-free means of improving athletic performance and strength. Increasing the creatine in a diet may therefore be useful to increase the blood plasma level of creatine and thus increase the amount of creatine in the muscles.

Creatine monohydrate is most commonly sold as a nutritional supplement in powder form. The powder may be blended with juices or other fluids, and then ingested. Prompt ingestion is important, because creatine is not stable in acidic solutions, such as juices. If creatine is retained in acidic solutions for even relatively short periods of time, most or all of the creatine in this solution converts to creatinine, which does not have the beneficial effects of creatine.

Creatine monohydrate supplementation at a dosage of 20 grams per day for a 5 day period has been the standard used during most studies in humans. Conventionally, creatine monohydrate is dissolved in approximately 300 milliliters of warm to hot water, the increased water temperature thereby increasing the solubility of creatine monohydrate. It has been found that creatine is not decomposed in the alimentary tract after oral administration, since there is no appreciable increase in urinary urea or ammonia. The results obtained for the conversion of retained creatine to creatinine have led researchers to believe that creatine is completely absorbed from the alimentary tract, then carried to the tissues, and hence either stored in the tissues or immediately rejected and eliminated by way of the kidneys.

Another problem with existing creatine supplementation is in the ability to provide consistent uniform results. It is believed that these inconsistent results arise because of the current methods of delivering creatine to the human body area. Current creatine oral supplementation, as discussed above relies on the use of creatine in powder form, which is dissolved in water and then taken orally. However, creatine in powder form does not dissolve well in water or other neutral pH liquids. The solubility of creatine in water is low, about 1 g in 75 ml. To obtain 10 grams, a subject would have to consume almost a liter of liquid. While increasing the temperature of the water increases the solubility of creatine monohydrate, there still is no consistency in the amount of creatine that is effectively dissolved in the water. For this reason, the consumer will take in varying amounts of creatine when consuming creatine monohydrate powder dissolved in water or other liquids.

Furthermore, the half-life of creatine in blood plasma is short (1–1.5 hours). This makes it necessary to reach high blood plasma levels rapidly. In view of the bioavailability of creatine, such blood plasma levels can be obtained only by the administration of high doses of creatine, e.g. 5–10 g for mean body weights of about 70 kg. Such high amounts are well tolerated because the toxicity of creatine is quite low.

Creatine monohydrate can be used to manufacture various salts. U.S. Pat. No. 5,973,199 (hereinafter "the '199 patent") discloses a creatine salts having the general formula:

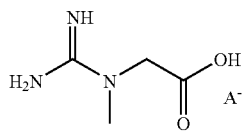

where A represents an anion of citric acid, maleic acid, fumaric acid, malic acid or tartaric acid. A molar excess of creatine, such as would be needed to make dicreatine salts, is not disclosed.

U.S. Pat. No. 5,925,378 (hereinafter the '378 patent) discloses an effervescent form of creatine comprising a tablet of creatine citrate, citric acid, sodium carbonate, sodium bicarbonate, dextrose and other ingredients. There is no disclosure or suggestion that the creatine citrate comprises anything other than a one-to-one molar ratio of creatine and citrate anion, as in the '199 patent.

It would be desirable to provide another form of creatine salt that is stable, and that can prevent or impede the conversion of creatine to creatinine, and which can provide multiple moles of creatine per mole of acid.

SUMMARY OF THE INVENTION

The embodiments provide creatine salts of the general formula:

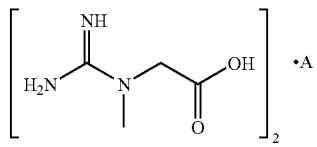

wherein A represents an anion of a dicarboxylic acid.

In one embodiment, A is an anion of maleic acid. In another embodiment, A in an anion of malic acid. The compounds of the embodiments are characterized by having 2 molecules of creatine per molecule of anion.

Another embodiment provides a process of making these creatine salts.

DETAILED DESCRIPTION

This disclosure provides a description of certain embodiments of the invention to further an understanding of the invention. It is to be understood that both the foregoing general description and the following detailed description are exemplary and explanatory only and are intended to provide further explanation of the present invention, as claimed.

The embodiments provide hydrosoluble, stable organic salts of creatine characterized by high water solubility and a process for preparing these salts. The creatine salts comprise two molecules of creatine and one molecule of anion derived from a dicarboxylic acid. Suitable dicarboxylic acids include malic acid, fumaric acid, maleic acid, and tartaric acid.

The salts of are prepared by salifying creatine with the corresponding organic acids in aqueous or preferably alcohol concentrated solution or in a water miscible solvent, at temperatures ranging from room temperature to 50° C., optionally concentrating the solutions, and filtering the crystallized salts. In the embodiments the compounds are prepared by reacting a molar excess of creatine with an organic dicarboxylic acid in a suitable solvent, until the compound is completely formed, cooling and filtering the resulting compound. The filtrated solvent may be recycled and used for a further reaction. The molar excess of creatine to carboxylic acid will be in a ratio of at least 2:1.

Any food grade form of the constituent compounds may be used in the process. Creatine monohydrate or anhydrous creatine may be employed to advantage as reactants. Similarly, food grade forms of maleic acid, malic acid, fumaric acid and tartaric acid may be employed.

EXAMPLE 1

Large scale quantities of the dicreatine maleate may be made in a batch process in the following manner.

A reactor is charged with 2,400 gallons of anhydrous methanol. With stirring, 781 kilograms (6,845 moles) of maleic acid is added to the methanol. Any suitable food grade maleic acid may be used. Stirring should continue until all of the maleic acid is dissolved.

Thereafter, with continued agitation, creatine monohydrate is added to the methanol/maleic acid mixture. Any suitable food grade creatine monohydrate may be used. One such creatine is available as Catalog No. C-114 from Pfanstiehl Laboratories, Waukegan, Ill. In this embodiment, at least 2050 kg of the creatine monohydrate is added to achieve at least a 2:1 molar ratio of creatine:maleic acid. Once all of the creatine monohydrate has been added, stirring should continue for approximately four (4) hours to allow the materials to react.

The finished product is dicreatine maleate, having two creatine molecules per maleate anion. The finished dicreatine maleate may be separated using crystallization, optionally preceded by distillation to concentrate the product. One skilled in the art will recognize other appropriate separation techniques that may be used to isolate the dicreatine maleate.

The crystallized dicreatine maleate product is filtered from the reaction mixture and collected. The filtrate is washed with anhydrous methanol to remove any byproducts or other impurities. The solid dicreatine maleate product is dried at a suitable temperature. The resulting crystalline material is ground to a free flowing consistency and packaged. If appropriate, suitable flavors and sweeteners may be added. The creatine content of the product is approximately 70% on a weight basis.

EXAMPLE 2

Dicreatine malate may be manufactured using a similar procedure but substituting malic acid for maleic acid. An exemplary bench-scale procedure is set forth below.

Five liters of anhydrous methanol are charged to a clean reactor. With stirring, 350 grams of anhydrous malic acid (2.6 moles) is added to the anhydrous methanol. The resulting mixture is stirred until dissolution is complete. Then, at least 775 grams (5.2 moles) of creatine monohydrate is added to the malic acid/methanol mixture. This mixture is stirred for approximately four (4) hours.

After the four hours have passed, the product is filtered and washed with anhydrous methanol. The finished product is dried. The product is approximately 66% creatine on a weight basis.

EXAMPLE 3

Example 2 is repeated, except that tartaric acid is substituted for malic acid. The quantities of tartaric acid and creatine are adjusted to provide at least creatine in a molar excess of at least 2:1.

EXAMPLE 4

Example 2 is repeated using fumaric acid in lieu of the malic acid and adjusting the quantities of fumaric acid and creatine to provide at least a 2:1 molar excess of creatine.

While the specific embodiments have been illustrated and described, numerous modifications may be made without significantly departing from the spirit and scope of the invention.

I claim:

1. A creatine salt having the formula

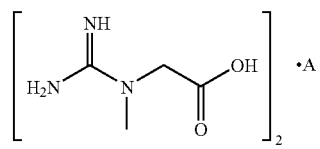

wherein A represents an anion of a dicarboxylic acid.

2. The creatine salt of claim 1, wherein A is an anion of maleic acid, malic acid, fumaric acid, or tartaric acid.

3. The creatine salt of claim 1, wherein A is an anion of malic acid.

4. The creatine salt of claim 1, wherein A is an anion of maleic acid.

5. The creatine salt of claim 1, wherein A is an anion of fumaric acid.

6. The creatine salt of claim 1, wherein A is an anion of tartaric acid.

7. A process comprising reacting a molar excess of creatine monohydrate and a dicarboxylic acid or a tricarboxylic acid with heat to form a creatine salt having the formula:

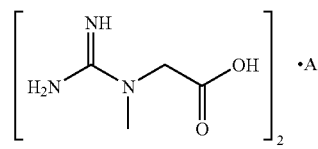

wherein A represents an anion of a dicarboxylic acid.

8. The process of claim 7, wherein the reaction is carried out in an alcohol solvent.

9. The process of claim 7, further comprising separating and drying the creatine salt.

10. The process of claim 7, wherein A is an anion of malic acid.

11. The process of claim 7, wherein A is an anion of maleic acid.

12. The process of claim 7, wherein A is an anion of fumaric acid.

13. The process of claim 7, wherein A is an anion of tartaric acid.

* * * * *